United States Patent
Park et al.

(10) Patent No.: US 10,583,163 B2
(45) Date of Patent: Mar. 10, 2020

(54) COMPOSITION FOR PREVENTION, ALLEVIATION OR TREATMENT OF PRECOCIOUS PUBERTY CONTAINING EXTRACT OF COICIS SEMEN AND ARTEMISIA CAPILLARIS AS ACTIVE INGREDIENT

(71) Applicant: Seung Chan Park, Daejeon (KR)

(72) Inventors: Seung Chan Park, Daejeon (KR); Hwa Seung Yoo, Daejeon (KR); Hye Lim Lee, Bucheon-si (KR)

(73) Assignee: Seung Chan Park, Daejeon (KR)

( * ) Notice: Subject to any disclaimer, the term of this patent is extended or adjusted under 35 U.S.C. 154(b) by 0 days.

(21) Appl. No.: 15/922,928

(22) Filed: Mar. 16, 2018

(65) Prior Publication Data

US 2018/0264069 A1 Sep. 20, 2018

(30) Foreign Application Priority Data

Mar. 16, 2017 (KR) .................. 10-2017-0032976

(51) Int. Cl.
*A61K 36/8994* (2006.01)
*A61K 36/282* (2006.01)
*A23L 33/105* (2016.01)
*A61P 5/08* (2006.01)

(52) U.S. Cl.
CPC ........ *A61K 36/8994* (2013.01); *A23L 33/105* (2016.08); *A61K 36/282* (2013.01); *A61P 5/08* (2018.01); *A61K 2236/331* (2013.01); *A61K 2300/00* (2013.01)

(58) Field of Classification Search
CPC . A61K 36/282; A61K 36/8994; A23L 33/105; A61P 5/08
See application file for complete search history.

(56) References Cited

FOREIGN PATENT DOCUMENTS

| JP | 11-228436 A | 8/1999 |
| KR | 10-0601265 B1 | 4/2004 |
| KR | 10-1626938 B1 | 6/2016 |
| KR | 10-1626941 B1 | 6/2016 |

OTHER PUBLICATIONS

Trinh TA, et al "Preventive Effect and Safety of a Follicle Stimulating Hormone Inhibitory Formulation Containing a Mixture of Coicis Semen and Artemisia capillaris for Precocious Puberty: A Prelim. Exper. Study Using Female Rats" Evid-Based Compl.Alt. Med., 2017, 8p.;doi:10.1155/2017/2906014. (Year: 2017).*
Lee HL; Lee YB; Choi J-Y; Lee, JA "Herbal medicine for idiopathic central precocious puberty: A protocol for a systematic review of controlled trials" Medicine, 2018 (pub. online Mar. 30, 2018) ,97 (13), e0267, pp. 1-3; PMID: 29595688; doi: 10.1097/MD. 0000000000010267. (Year: 2018).*

* cited by examiner

Primary Examiner — Aaron J Kosar
(74) Attorney, Agent, or Firm — Revolution IP, PLLC

(57) ABSTRACT

A pharmaceutical composition and a food composition for preventing, alleviating or treating precocious puberty, which contain, as an active ingredient, a hot-water extract of *Coicis* Semen and *Artemisia capillaris*, which inhibits early ovary growth and the production of follicle-stimulating hormone. The composition contains a hot-water extract of *Coicis* Semen and *Artemisia capillaris*, which can inhibit early ovary growth and follicle stimulating hormone production, thereby preventing, alleviating or treating precocious puberty.

6 Claims, 21 Drawing Sheets

COMPOSITION FOR PREVENTION, ALLEVIATION OR TREATMENT OF PRECOCIOUS PUBERTY CONTAINING EXTRACT OF COICIS SEMEN AND ARTEMISIA CAPILLARIS AS ACTIVE INGREDIENT

BACKGROUND OF THE INVENTION

Field of the Invention

The present invention relates to a composition for preventing, alleviating or treating precocious puberty, which contains an extract of *Coicis* Semen and *Artemisia capillaris* as an active ingredient, and more specifically to a pharmaceutical composition and a food composition for preventing, alleviating or treating precocious puberty, which contains, as an active ingredient, an extract of *Coicis* Semen and *Artemisia capillaris*, which inhibits early ovary growth and the production of follicle stimulating hormone.

Description of the Prior Art

Precocious puberty is a phenomenon in which secondary sexual characteristics such as breast development and testis enlargement early appear. These anomalies are pointed out as factors that not only hinder the growth of children, but also cause stress. Sexual maturation is initiated by the secretion of sexual hormones caused by gonadotropic hormone (GTH) secreted from hypophysis (pituitary gland), and the age at menarche has been steadily decreasing. The date released by the Korea National Statistical Office showed that the average age of menarche of women in Korea was 14.4 years in 1970, but was 11.98 in 2009. Recent studies have shown that women who have experienced menarche before 12 years of age have a 1.57-fold greater risk of breast cancer than women who do not have it, and more hormones are accumulated in the breast or endometrium as the duration of exposure to female hormones such as estrogen becomes longer, thus increasing the risk of cancer. According to the statistics of the Health Insurance Review & Assessment Service, the number of patients who visit hospitals for precocious puberty is greatly increasing, and the number of patients who have received medication increased from 587 in 2006 to 2770 in 2010 and was 10 times larger in girls than in boys.

It is known that although precocious puberty may be caused by organic causes such as central nervous system tumors or brain injury, other factors, including excessive sex hormone secretion, obesity due to excessive nutrition, stress, environmental changes and the like, may also contribute to precocious puberty. People who visit hospitals due to concerns about early sexual maturation, although not diagnosed as precocious puberty, are increasing. In addition, when people are treated for short stature, they want to improve their growth without advancing maturity. Parents' greatest concerns about puberty starting early is that the growth plate closes early so that growth is prematurely terminated, resulting in disadvantages in terms of the final height. In addition, when people receive treatment for growth, their parents may be worried about whether or not the treatment advances maturity.

Several factors are involved in precocious puberty. The first of these is a genetic factor. If the breast of the mother developed early, the breast of the daughter may also develop early. In addition, Westernized eating habits, obesity, stress and the like are known to be involved in precocious puberty. There was also debate about the role of many environmental chemicals in precocious puberty. For example, dioxin generated during waste incineration, and phthalate and BPA contained in plastic products, cause hormone-like effects. These compounds, when accumulated in the body, act like sex hormones to promote sexual maturity. In particular, rapid growth of more than 4 cm within 6 months should be regarded as an abnormal case.

Patients with suspected precocious puberty may need to be examined through a medical check-up to see if the start time of second sexual development is less than 8 years for girls and less than 9 years for boys. Through gonadotropin releasing hormone (GnRH) stimulation tests, pseudoprecocious puberty and true precocious puberty can be distinguished. In true precocious puberty, both gonadotropin and gonadal steroid appear at high concentrations, whereas, in pseudoprecocious puberty, only gonadal steroid appears at high concentration. If the maximum value of LH after GnRH stimulation is 5 mIU/ml or more, it can be diagnosed as true precocious puberty.

A gonadotropin releasing hormone agonist (GnRHa), which is used as a drug for the treatment of precocious puberty, is synthesized to have a potency that is 20 to 150 times higher than that of GnRH present in the human body. It acts as a mechanism to down-regulate GnRH receptor expression in the pituitary gland to thereby inhibit gonadotropin secretion. The treatment effect on GnRHa greatly varies depending on individuals. Factors known to affect the final height include the duration of treatment, the period from onset to treatment initiation, the age at the onset of treatment, and the progression of bone age vs. chronological age. Treatment of precocious puberty should be continued for at least 2 years and is stopped when the bone age reaches about 12 years. In the case of these true precocious puberty patients, it is known that when treatment of precocious puberty is started at 6-7 years of age after early diagnosis, the final height is increased by about 5-10 cm, but when the treatment is started after 9 years of age, it is ineffective. As a side effect, aseptic abscess may occur in about 5% of the patients. In addition, it was reported that hypersensitivity reactions, granuloma at the injection site, femoral head separation, reduced bone density and the like rarely occurred. Due to concerns about the adverse effects of the GnRH agonist, parents are increasingly seeking to treat precocious puberty using herbal medicines. However, these herbal medicines are confusing to parents, because it is not ensured that their effects were objectively verified. Accordingly, the present inventors have made efforts for many years to develop a new and effective drug from materials that can be used in herbal medicine based on objective verification of the therapeutic effects of these materials on precocious puberty. As a result of these studies, the present inventors got a patent about a composition for preventing or alleviating precocious puberty as disclosed in Korean Patent No. 10-1626938. Without stopping here, the present inventors have made efforts to develop a more effective drug, and as a result, have found that a hot-water extract of *Coicis* Semen and *Artemisia capillaris* is more effective for the prevention, alleviation or treatment of precocious puberty and is also helpful in height growth, thereby completing the present invention.

PRIOR ART DOCUMENTS

Patent Documents

Korean Patent No. 10-1626938.

SUMMARY OF THE INVENTION

Therefore, it is a main object of the present invention to provide a composition which has an excellent effect on the prevention, alleviation or treatment of precocious puberty, and which eliminates the need to worry about side effects by using an extract of plants which have been widely used as herbal medicines and have been proved to be safe for the human body.

In one aspect, the present invention provides a pharmaceutical composition for preventing or treating precocious puberty, which contains, as an active ingredient, a hot-water extract of *Coicis* Semen and *Artemisia capillaris*.

In the pharmaceutical composition of the present invention, the hot-water extract is preferably prepared by adding a 10-20-fold weight of water to *Coicis* Semen and *Artemisia capillaris* mixed at a weight ratio of 2:3 to 3:2, thereby obtaining a mixture, and extracting the mixture at a temperature of 80 to 110° C. for 2 to 4 hours, followed by concentration.

In the pharmaceutical composition of the present invention, the composition inhibits early ovary growth, inhibits the production of follicle-stimulating hormone, and increases body length.

In another aspect, the present invention provides a food composition for preventing or alleviating precocious puberty, which contains, as an active ingredient, a hot-water extract of *Coicis* Semen and *Artemisia capillaris*.

In the food composition of the present invention, the hot-water extract is preferably prepared by adding a 10-20-fold weight of water to *Coicis* Semen and *Artemisia capillaris* mixed at a weight ratio of 2:3 to 3:2, thereby obtaining a mixture, and extracting the mixture at a temperature of 80 to 110° C. for 2 to 4 hours, followed by concentration.

In the food composition of the present invention, the composition inhibits early ovary growth, inhibits the production of follicle-stimulating hormone, and increases body length.

DETAILED DESCRIPTION OF THE INVENTION

Figure 1:
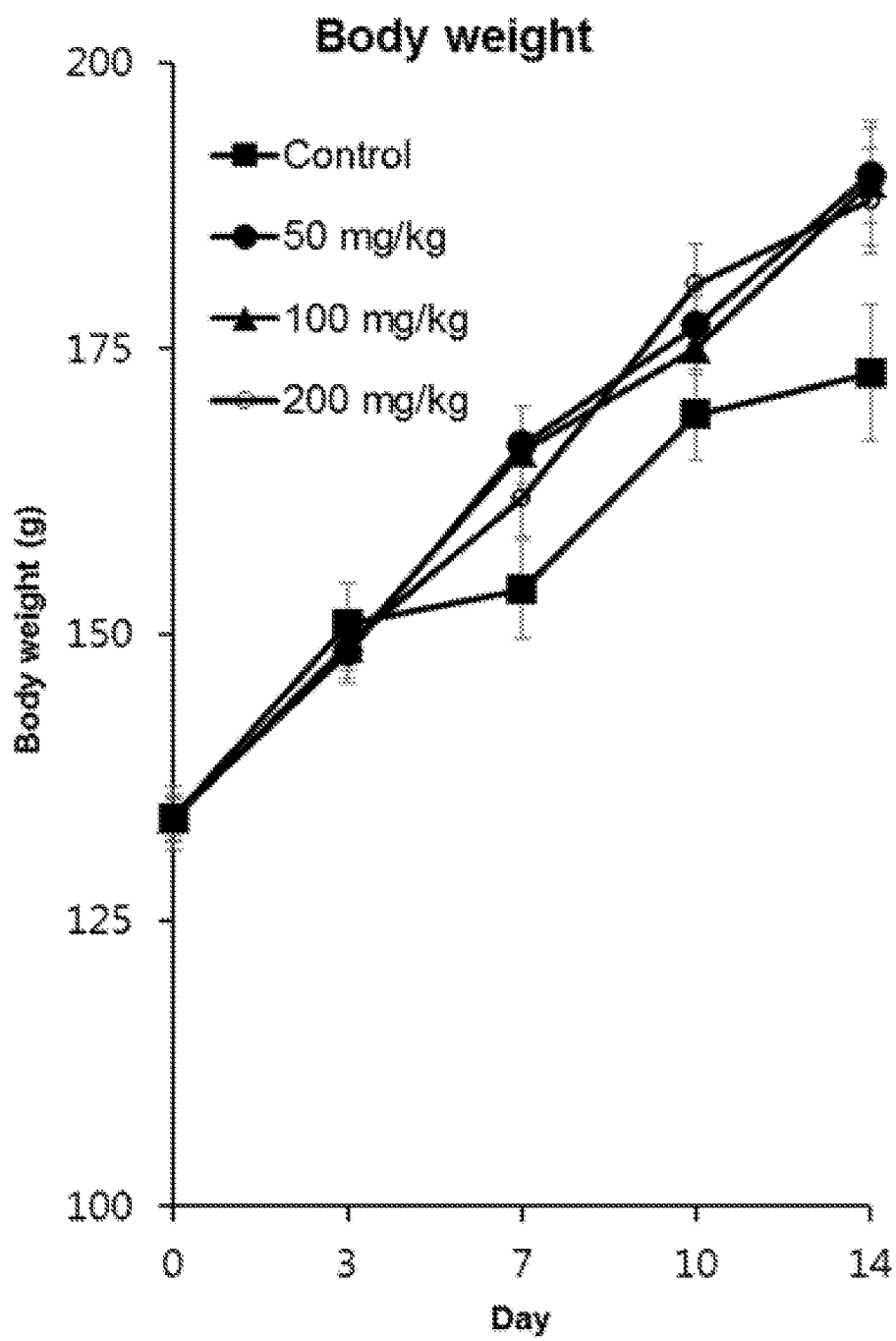
FIG. 1 shows the results of examining the effect of the extract of the present invention on body weight.

The composition according to the present invention is characterized by containing a hot-water extract of *Coicis* Semen and *Artemisia capillaris* as an active ingredient.

*Coicis* Semen is the well ripe seed of *Coix lacryma-jobi* L. var. *ma-yuen* Stapf belonging to the family Gramineae, from which the seed husk was removed. It is drunk as tea, or is used as a medicine for edema, neuralgia, rheumatism, bladder stones and the like, because it has diuretic, analgesic and tonic activities.

*Artemisia capillaris* is the aerial part of *Artemisia capillaris* Thunberg belonging to the family Compositae. *Artemisia capillaris* was reported to have effects, including bile secretion promotion, liver function protection, liver cell regeneration, lipid degradation, coronary artery dilatation, blood pressure lowering, antipyretic, diuretic, antimicrobial, and ascites cancer cell inhibitory effects.

The hot-water extract according to the present invention may be prepared by adding water to *Coicis* Semen and *Artemisia capillaris*, followed by heating. In the extraction process, the extracted components vary depending on various conditions, including the ratio between the materials used, the kind of extraction solvent, the amount of extraction solvent used, extraction temperature, extraction time, and the like, and thus the effects of the present invention may depend on such conditions. According to the present invention, water is added to *Coicis* Semen and *Artemisia capillaris* (mixed at a weight ratio of 2:3 to 3:2) in an amount equal to 10-20 times the total weight of the two herbal plants to obtain a mixture, and the mixture is extracted at a temperature of 80 to 110° C. for 2 to 4 hours. In this case, an extract having the effect of preventing, alleviating or treating precocious puberty can be obtained. More preferably, water is added to *Coicis* Semen and *Artemisia capillaris* (mixed at a weight ratio of 4:5 to 5:4) in an amount equal to 13-17 times the total weight of the two herbal plants to obtain a mixture, and the mixture is extracted at a temperature of 90 to 110° C. Although the hot-water extract prepared under such extraction conditions may be used without further treatment, it is preferably subjected to filtration and concentration processes in order to facilitate administration, intake or formulation. In this case, the filtration may be performed by a conventional filtration method using a filter or the like in order to remove extraction meal of the *Coicis* Semen and *Artemisia capillaris* used as extraction materials and to remove other solid impurities. The concentration may be performed by a conventional concentration method in order to remove water used as the extraction solvent. The concentration is preferably performed at a temperature of 60° C. or below in order to prevent the destruction or degeneration of active components contained in the extract.

In the present invention, it was proved through animal experiments that the hot-water extract of *Coicis* Semen and *Artemisia capillaris* as described above can inhibit early ovary growth and the production of follicle-stimulating hormone (FSH).

A comparison between a group treated with the extract of the present invention and a control group indicated that the ovary weight in the treated group significantly decreased, whereas changes in the weights of other organs including spleen were not significant. This suggests that the extract of the present invention can prevent, alleviate and treat precocious puberty by inhibiting early ovary growth.

Furthermore, the concentration of FSH that is a kind of gonadotropin significantly decreased in the treated group in a concentration-dependent manner. FSH is a hormone playing a very important role in sexual maturation, stimulates ovary growth and estrogen production, and also stimulates spermatogenesis in males. In precocious puberty, the level of this hormone reaches the level at puberty at an early age, and thus early sexual maturation occurs. The extract of the present invention can inhibit the production of this FSH, thereby preventing, alleviating and treating precocious puberty. It appears that the effect of inhibiting FSH production is associated with the effect of inhibiting early ovary growth as described above. In addition, it was shown that estradiol decreased in a concentration-dependent manner, although this decrease was not significant. This decrease in estradiol also appears to be associated with the effect of inhibiting FSH production.

The extract of the present invention showed no significant change in body weight, but showed a significant increase in body length. This result suggests that the extract of the present invention can promote height growth, in addition to having the effect of preventing, alleviating or treating precocious puberty as described above. This effect of promoting height growth can be a very big advantage.

The concentration of osteocalcin that is a protein closely associated with bone formation also significantly increased in the treated group, suggesting that the extract of the present invention assists in bone formation. The plasma osteocalcin concentration suggests the activity of osteoblasts, and a high blood concentration of osteocalcin is very highly correlated with an increase in bone mineral density (BMD). The effect of the extract of the present invention on osteocalcin as described above appears to be associated also with the increase in body length.

The pharmaceutical composition of the present invention may contain the extract of the present invention in an amount of 0.1 to 100 wt % based on the total weight of the composition.

The pharmaceutical composition of the present invention may be administered orally or parenterally in clinical practice, but is preferably administered orally. When the pharmaceutical composition is administered parenterally, it may be administered by intraperitoneal, intrarectal, subcutaneous, intravenous, intramuscular, intradural, intracerebral or intrathoracic injection, and may be used in the form of a general medical formulation.

It is understood that the pharmaceutical composition of the present invention may be used alone or in combination with surgery, radiotherapy, hormonal therapy, chemotherapy or a biological response regulator.

The daily dose of the pharmaceutical composition according to the present invention may be 0.001 to 10 mg/kg, preferably 0.01 to 1 mg/kg, as calculated on the basis of the dry weight of the extract contained in the composition, and may be administered once or several times a day. However, the daily dose may vary depending on the patient's weight, age, sex, health condition, diet, the time of administration, the mode of administration, excretion rate, and the severity of the disease.

The pharmaceutical composition of the present invention may be administered as various formulations in actual clinical practice. It may be formulated using diluents or excipients, including fillers, extenders, binders, wetting agents, disintegrants and surfactants, which are commonly used. Formulations for parenteral administration include sterile aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, and the like may be used. As the base of the suppositories, witepsol, Macrogol, Tween 61, cacao butter, laurin fat, glycerogelatin and the like may be used.

The pharmaceutical composition of the present invention may further contain, in addition to the extract of the present invention, one or more active ingredients showing the same or similar function.

The food composition of the present invention may comprise an effective amount of the extract of the present invention alone or in a mixture with a food-acceptable carrier. It is understood that the food composition of the present invention may be in the form of processed meat products, fish meat products, Tofu, jelly, porridge, noodles such as Ramen or Udon, seasoning foods such as soy sauce, soybean paste, red pepper paste or mixed soybean pastes, sauces, confectionery, dairy products such as fermented milk or cheese, pickled foods such as kimchi and pickles, fruits, vegetables, beverages such as fermented beverages, and the like. In addition, as the food-acceptable carrier, the pharmaceutically acceptable carrier as descried above may also be used.

Hereinafter, the present invention will be described in further detail with reference to examples. It is to be understood, however, that these examples are for illustrative purposes only and are not intended to limit the scope of the present invention.

Example 1: Preparation of Extract 600 g of selected *Coicis* Semen and 600 g of selected *Artemisia capillaris* were placed in an extractor, and tap water or purified water was added thereto in an amount equal to about 15 times the total weight of the two herbal plants. Next, the herbal extracts were extracted at about 100° C. for about 3 hours, thereby obtaining an extract. The extract was filtered through a 1-micron filter, and the filtrate was concentrated under reduced pressure at a temperature of 60° C. or below and dried, thereby obtaining 103.8 g of a dry extract (yield: 8.65%).

Test Example 1: Animal Test

1. Test Method 1-1. Test Animals and Test Design

Using specified-pathogen-free Sprague-Dawley rats (average weight: 110 g; age: 4 to 5 weeks), the effect of the extract of Example 1 on precocious puberty was tested for 3 weeks.

A solution of the extract in 1 ml of water was administered orally to the white rats of test groups at doses of 50 mg/kg, 100 mg/kg and 200 mg/kg. The rats were divided into four groups, each consisting of five animals: a group administered with 50 mg/kg; a group administered with 100 mg/kg; a group administered with 200 mg/kg; and a control group. The test groups were administered with the indicated doses of the extract, and the control group was administered with water.

1-2: Measurement of Body Weight, Dietary Intake and Growth Index

During the test period, diet intake was calculated by measuring the amount of the remaining feed at the same time point on the day after feeding the feed daily, and the body weight gain of the rats was calculated by measuring the body weight of the rats at 1-week intervals. The body length of the rats was determined by fixing a tape measure on a test table, anesthetizing the rat with ethyl ether, and then measuring the length ranging from the nasal tip to the portion excluding the tail. The femur length of the rats was measured using calipers at the end of the test after the right femur was extracted and the muscle was removed.

1-3: Measurement of Weight of Organs

In order to examine the weight of organs, at the end of the test, blood was sampled, and then the rats were dissected to extract the liver, the kidney, the spleen and ovary. The organs were washed with saline, and then blood, body fluids and water in the organs were removed with gauze, after which the actual weights of the organs were measured.

1-4: Analysis of Blood Components

In order to examine blood components, at the end of the test, the test rats were anesthetized with ethyl ether, and then blood was sampled from the heart. The levels of glucose, cholesterol, calcium and the like in the serum were measured with an automatic chemical analyzer, and the blood ALP activity and the blood concentrations of estradiol, follicle-stimulating hormone, Luteinizing hormone, osteocalcin, IGF-1 and IGFBP-3 were analyzed by an enzymatic colorimetric method using a kit. The bone mineral density in the extracted femur was measured using a bone density meter.

1-5: Significance of Analysis of Blood Hormone Level and Bone Formation Index

1) Estradiol: it collectively refers to substances that cause estrous behavior in females and promote the development and function of accessory reproductive organs accompanied by estrus. It is also known as follicular hormone because it is secreted mainly from follicles.

2) Follicle-stimulating hormone (FSH): It is a kind of gonadotropin secreted from the gonadal cells of the anterior pituitary gland. It is a glycoprotein hormone and is regulated by the gonadotropin releasing hormone (GnRH) secreted from the hypothalamus. It stimulates the growth and maturation of follicles in the ovary in the female, promotes the differentiation of germinal cells in the convoluted seminiferous tubule of the testes in males, and promotes development into secondary spermatocytes during spermatogenesis.

3) Luteinizing hormone (LH): It is a type of gonadotropin secreted from the gonadal cells of the anterior pituitary gland, like FSH, and is a glycoprotein hormone. It co-acts with FSH in females to fully develop follicles and secrete a large amount of estrogen. In males, it stimulates interstitial cells in the testes and secretes androgens.

4) Osteocalcin: It is a bone formation biomarker and is a skeletal acidic protein containing γ-carboxyglutamic acid (Gla) found in prothrombin. It is produced inly in osteoblasts and odontoblasts. Osteocalcin synthesized by osteoblasts is deposited in bone cells along with apatite crystals and can also be observed in plasma (normal value: 6 to 7 ng/ml). Although the role of osteocalcin in the skeleton is unknown, the concentration of osteocalcin in plasma suggests the activity of osteoblasts, and the high concentration of osteocalcin in blood is very highly correlated with an increase in bone mineral density (BMD).

5) ALP (alkaline phosphatase): It is a bone formation biomarker secreted from osteoblasts. It is most commonly used as an bone formation index and is produced in bone. However, 50% or more of ALP is also produced in liver, kidney, placenta and the like, and thus its sensitivity and specificity are somewhat low. It is a phosphatase enzyme that releases inorganic phosphoric acid from organic phosphoric acid esters and is alkaline with an optimum pH of 9. Serum ALP activity is clinically examined because it changes by the disease of liver or bone. Alkaline phosphatase is the most abundant in bone and is also found in plasma. Plasma ALP is released from the liver in a normal state, and the activity of this enzyme increases in plasma in the case of obstructive jaundice. In addition, the activity of this enzyme increase in the case of rickets, hyperparathyroidism, Paget's disease, osteosarcoma, metastatic cancer and the like. Six ALP isozymes exist.

6) IGF-1 and IGFBP-3: GH (growth hormone) produces insulin-like growth factor-I (IGF-I) in liver and skeletal tissues to induce IGF-I to act on IGF-I cartilage tissue to thereby stimulate growth and increase protein anabolism. Insulin-like growth factor binding protein-3 (IGFBP-3) is directly affected by GH. IGFBP-3 binds to IGF-I and acid labile subunits (ALSs) to form a 150-kDa complex in blood.

IGF-I increases in the case of acromegaly, gigantism or hyperthyroidism, and decreases in the case of pituitary short stature, malnutrition, GH secretion dysfunction-mediated short stature, and delayed puberty. IGFBP-3 is a useful marker for adaptive assessment and monitoring in the diagnosis and treatment of GH deficiency. It increases in the case of acromegaly and decreases in GH deficiency.

1-6: Statistical Processing

Experimental results were expressed as mean±standard error. Statistical analysis was performed using Student's t-test or one-way ANOVA. P-values less than 0.05 were considered statistically significant.

2: Test Results 2-1: Body Weight and Daily Weight Gain

At the end of the test, the test groups (50 mg/kg, 100 mg/kg, and 200 mg/kg) showed body weights of 190.14±4.23 g, 189.46±5.40 g, and 187.94±4.56 g, respectively (see FIG. 1). In addition, the control group showed a body weight of 172.83±5.98 g. Thus, it could be seen that all the test groups increased body weights compared to the control group, but no significant difference in the body was observed.

2-2: Dietary Intake

Figure 2:
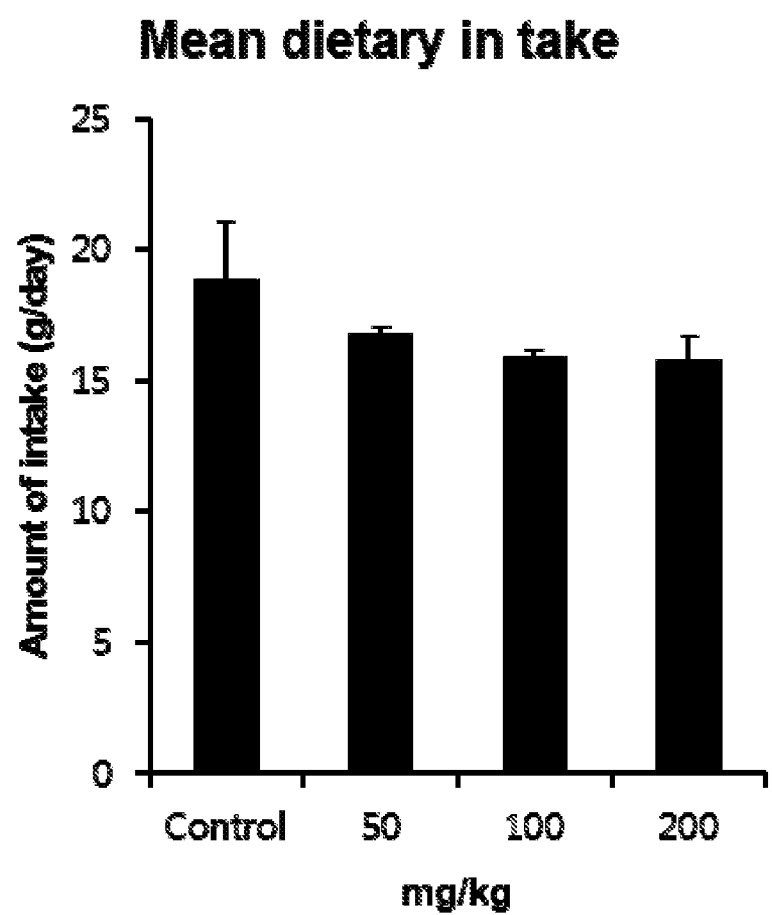
FIG. 2 shows the results of examining the effect of the extract of the present invention on dietary intake.

During the test period, the test groups (50 mg/kg, 100 mg/kg, and 200 mg/kg) showed mean dietary intakes of 16.73 g/day, 15.89 g/day, and 15.75 g/day, respectively (see FIG. 2). In addition, the control group showed a dietary intake of 18.85 g/day. Thus, it could be seen that the dietary intakes of the test groups somewhat decreased compared to that of the control group.

2-3: Body Length

Figure 3:
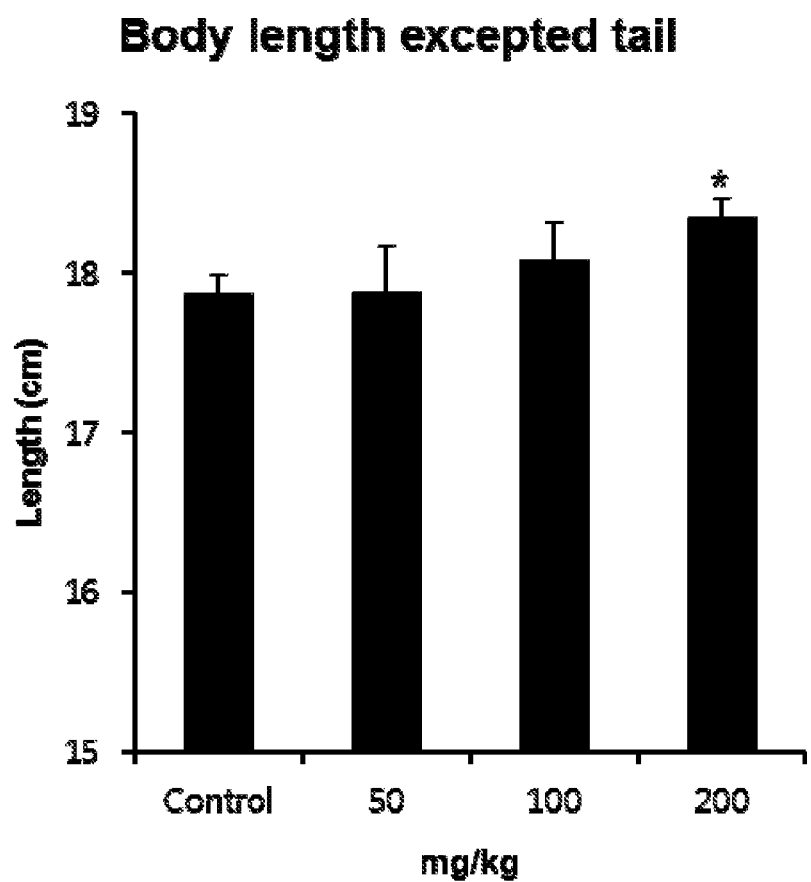
FIG. 3 shows the results of examining the effect of the extract of the present invention on body length (excluding tail) using rats as animal models.
Figure 4:
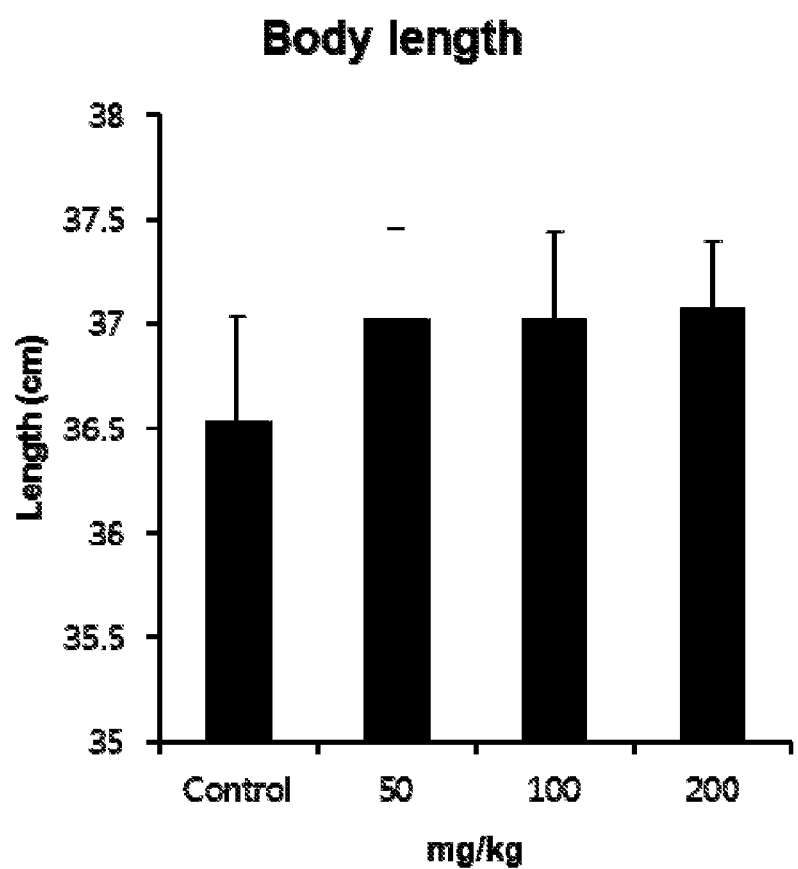
FIG. 4 shows the results of examining the effect of the extract of the present invention on body length (including tail) using rats as animal models.

At the end of the test, the body lengths excluding the tail in the test groups (50 mg/kg, 100 mg/kg, and 200 mg/kg) were 17.88±0.29 cm, 18.08±0.24 cm, and 18.34±0.14 cm, respectively (see FIG. 3). Furthermore, the body lengths including the tail in the test groups (50 mg/kg, 100 mg/kg, and 200 mg/kg) were 37.02±0.44 cm, 37.02±0.42 cm, and 37.08±0.32 cm (see FIG. 4). In addition, the body length excluding the tail and the body length including the tail in the control group were 17.87±0.13 cm and 36.53±0.50 cm, respectively. Thus, it could be seen that the body length excluding the tail in the group administered with 200 mg/kg significantly increased compared to that in the control group, and the body length including the tail in all the test groups also somewhat increased compared to that in the control group.

2-4: Femur Length

Figure 5:
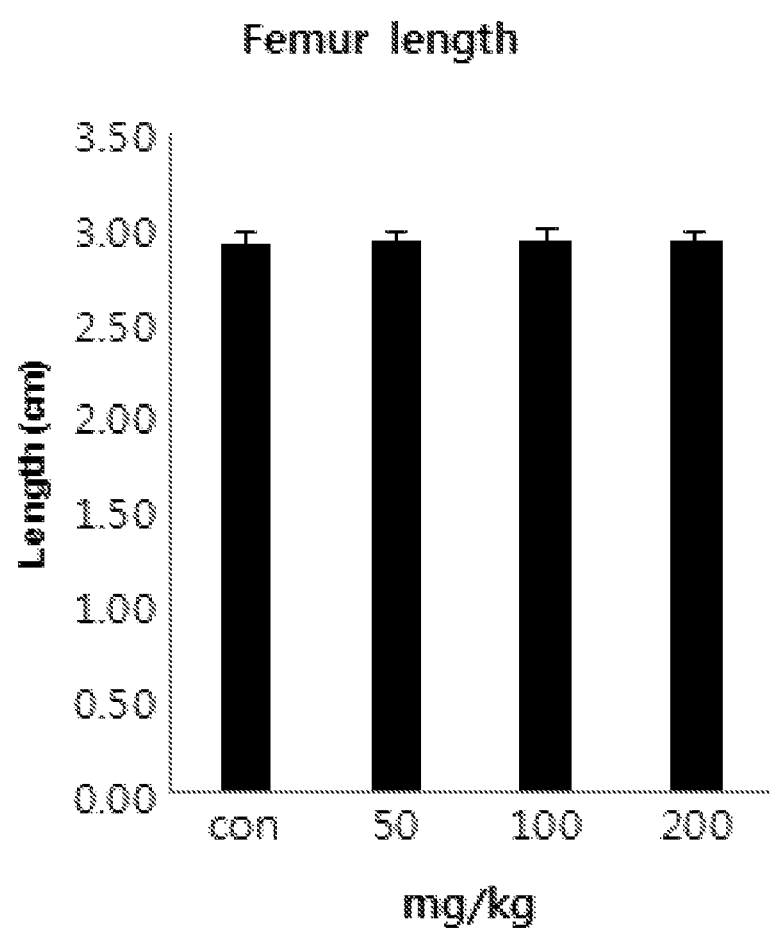
FIG. 5 shows the results of examining the effect of the extract of the present invention on femur length.

At the end of the test, the test groups (50 mg/kg, 100 mg/kg, and 200 mg/kg) showed femur lengths of 2.907±0.07 mm, 2.882±0.02 mm, 2.923±0.05 mm, respectively (see FIG. 5). The control group showed a femur length of 2.909±0.05 mm, which was little different from those of the test groups.

2-5: Femur Weight

Figure 6:
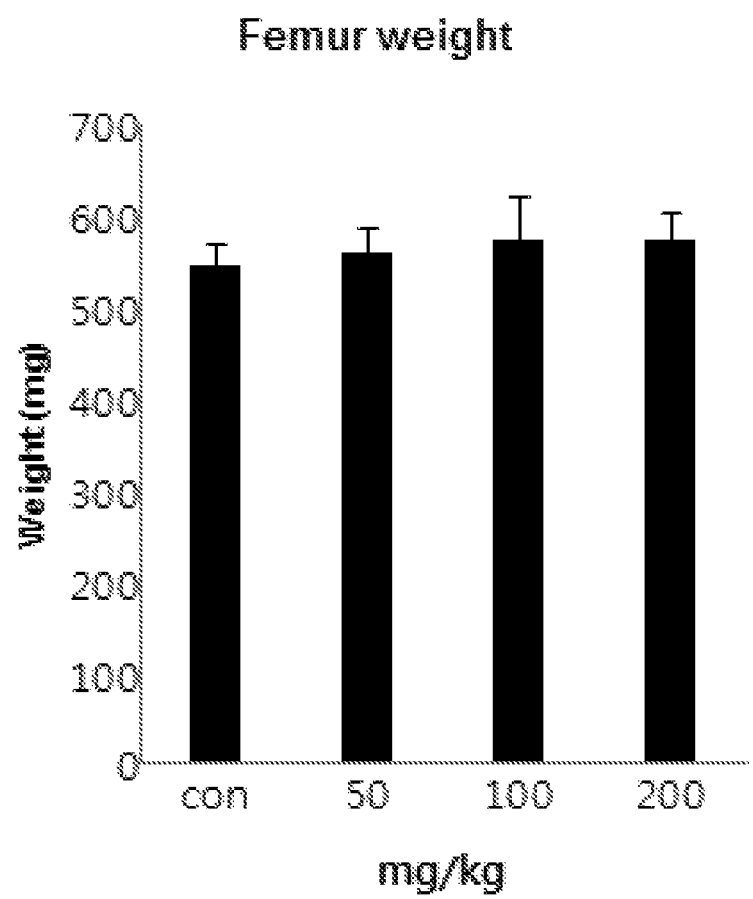
FIG. 6 shows the results of examining the effect of the extract of the present invention on femur weight.

At the end of the test, the test groups (50 mg/kg, 100 mg/kg, and 200 mg/kg) showed femur weights of 540.8±25.52 mg, 531.7±29.46 mg, and 544.8±28.37 mg, respectively (see FIG. 6). The control group showed a femur weight of 545.7±23.16 mg, which was not significantly different from those of the test groups.

2-6: Liver Weight

Figure 7:
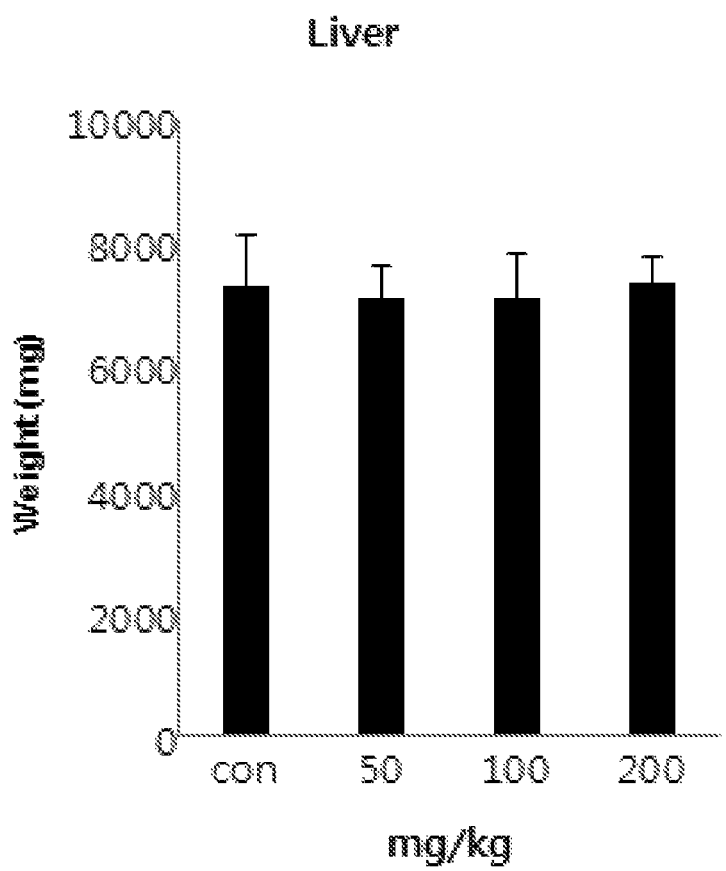
FIG. 7 shows the results of examining the effect of the extract of the present invention on liver weight.

At the end of the test, the test groups (50 mg/kg, 100 mg/kg, and 200 mg/kg) showed liver weights of 7419.8±25.52 mg, 7374.2±884.96 mg, and 6934±306.75 mg, respectively (see FIG. 7). The control group showed a liver weight of 7298.4±828.43 mg, which was not significantly different from those of the test groups.

2-7: Spleen Weight

Figure 8:
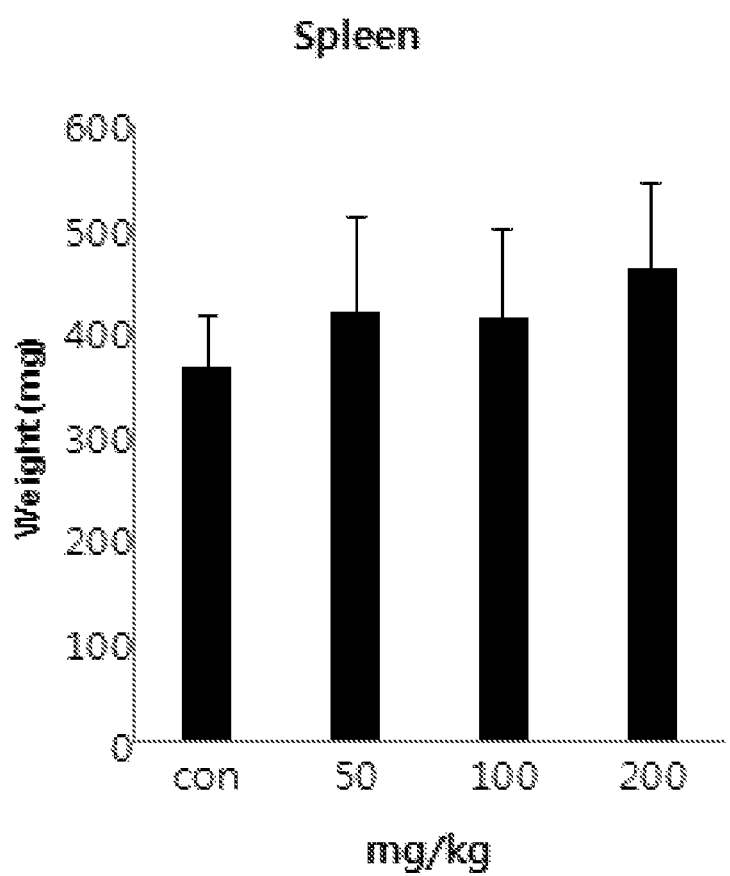
FIG. 8 shows the results of examining the effect of the extract of the present invention on spleen weight.

At the end of the test, the test groups (50 mg/kg, 100 mg/kg, and 200 mg/kg) showed spleen weights of 422.8±35.00 mg, 419.2±40.07 mg, and 385.8±36.16 mg, respectively (FIG. 8). The control group showed a spleen weight of 363.2±49.11 mg. It could be seen that the spleen weights of the test groups slightly increased compared to that of the control group, but this increase was not significant.

2-8: Kidney Weight

Figure 9:
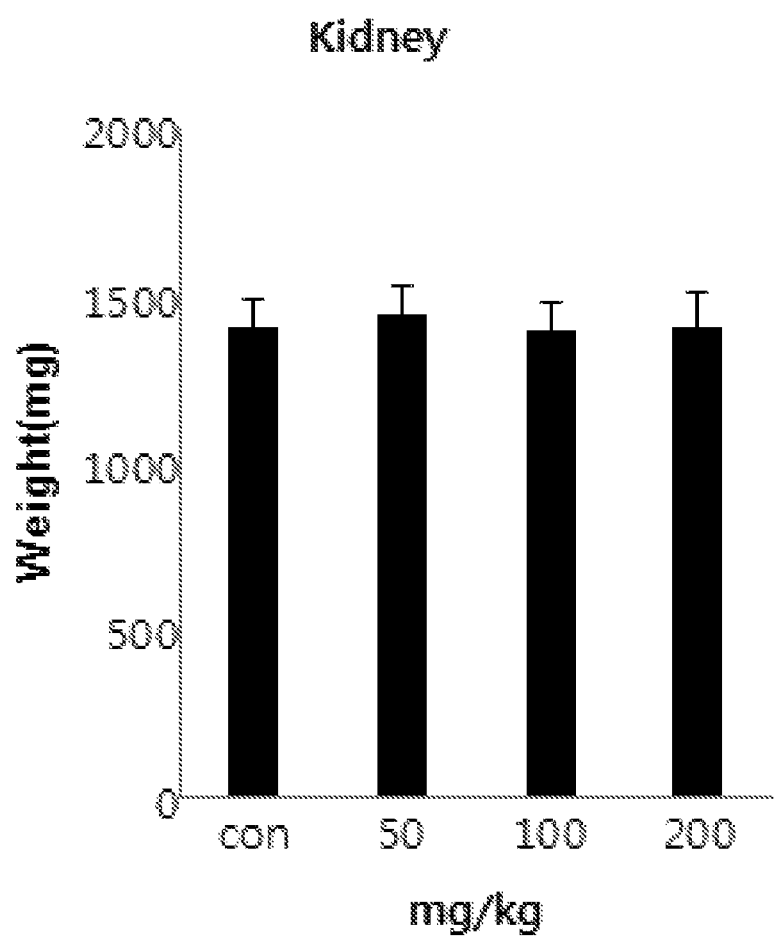
FIG. 9 shows the results of examining the effect of the extract of the present invention on kidney weight.

At the end of the test, the test groups (50 mg/kg, 100 mg/kg, and 200 mg/kg) showed kidney weights of 1394.8±57.29 mg, 1347.4±90.85 mg and 1320±84.10 mg, respectively (see FIG. 9). The control group showed a spleen weight of 1406±87.08 mg. It could be seen that the kidney weights of the test groups slightly decreased compared to that of the control group, but this decrease was not significant.

2-9: Ovary Weight

Figure 10:
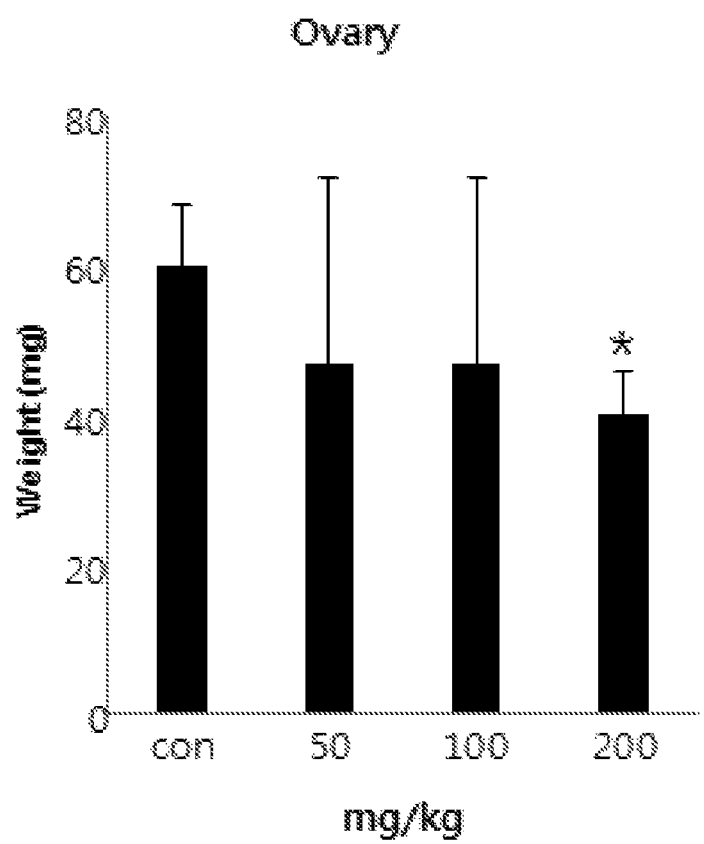
FIG. 10 shows the results of examining the effect of the extract of the present invention on ovary weight.

At the end of the test, the test groups (50 mg/kg, 100 mg/kg, and 200 mg/kg) showed ovary weights of 69.8±14.71 mg, 55.6±5.95 mg and 45±8.04 mg, respectively (see FIG. 10). The control group showed an ovary weight of 60±8.15 mg. Thus, it could be seen that the ovary weight generally decreased in the test groups, and significantly decreased in the group administered with 200 mg/kg of the extract.

2-10. Glucose

Figure 11:
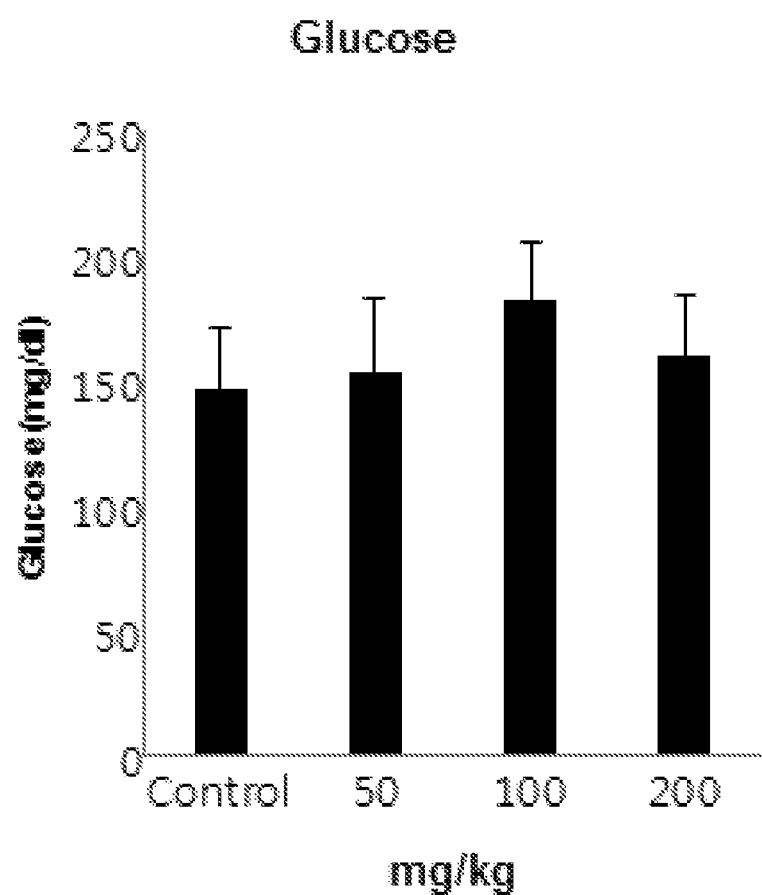
FIG. 11 shows the results of examining the effect of the extract of the present invention on blood glucose level.

The test groups (50 mg/kg, 100 mg/kg, and 200 mg/kg) showed glucose levels of 167.80±19.69 mg/dl, 158.80±19.40 mg/dl, and 175.80±16.74 mg/dl, respectively (see FIG. 11). The control group showed a glucose level of 147.00±24.24 mg/dl. Thus, it could be seen that the glucose level somewhat increased in the test groups compared to the control group.

2-11. TC (Total-Cholesterol)

Figure 12:
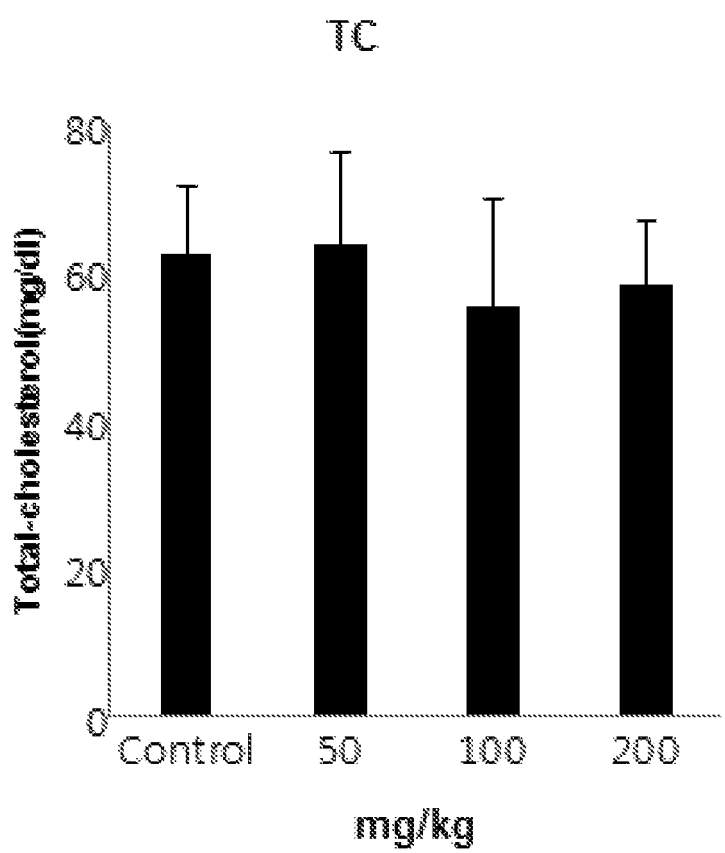
FIG. 12 shows the results of examining the effect of the extract of the present invention on blood total-cholesterol level.

The test groups (50 mg/kg, 100 mg/kg, and 200 mg/kg) showed TC levels of 60.80±7.26 mg/dl, 56.60±8.88 mg/dl and 67.80±10.83 mg/dl, respectively (see FIG. 12). The control group showed a TC level of 62.50±9.11 mg/dl. Thus, it could be seen that the TC level somewhat increased or decreased in the test groups compared to the control group.

2-12: Calcium

Figure 13:
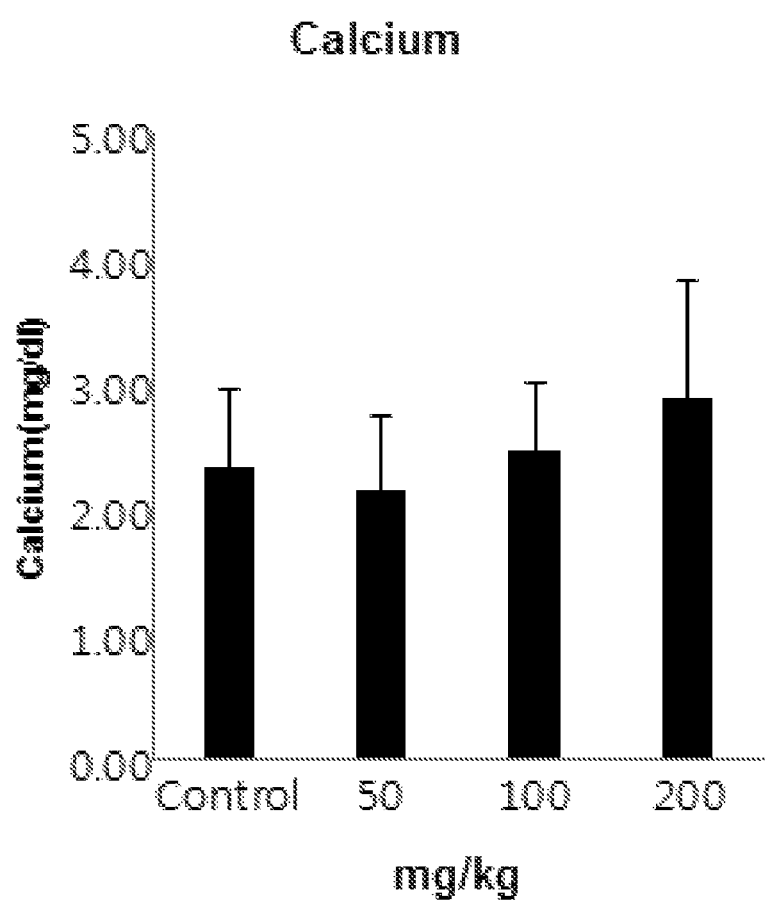
FIG. 13 shows the results of examining the effect of the extract of the present invention on blood calcium level.

The test groups (50 mg/kg, 100 mg/kg, and 200 mg/kg) showed calcium levels of 2.30±0.59 mg/dl, 2.38±0.65 mg/dl and 2.12±0.50 mg/dl, respectively (see FIG. 13). The control group showed a calcium level of 2.33±0.64 mg/dl, which was not significantly different from those of the test groups.

2-13: IGF-1

Figure 14:
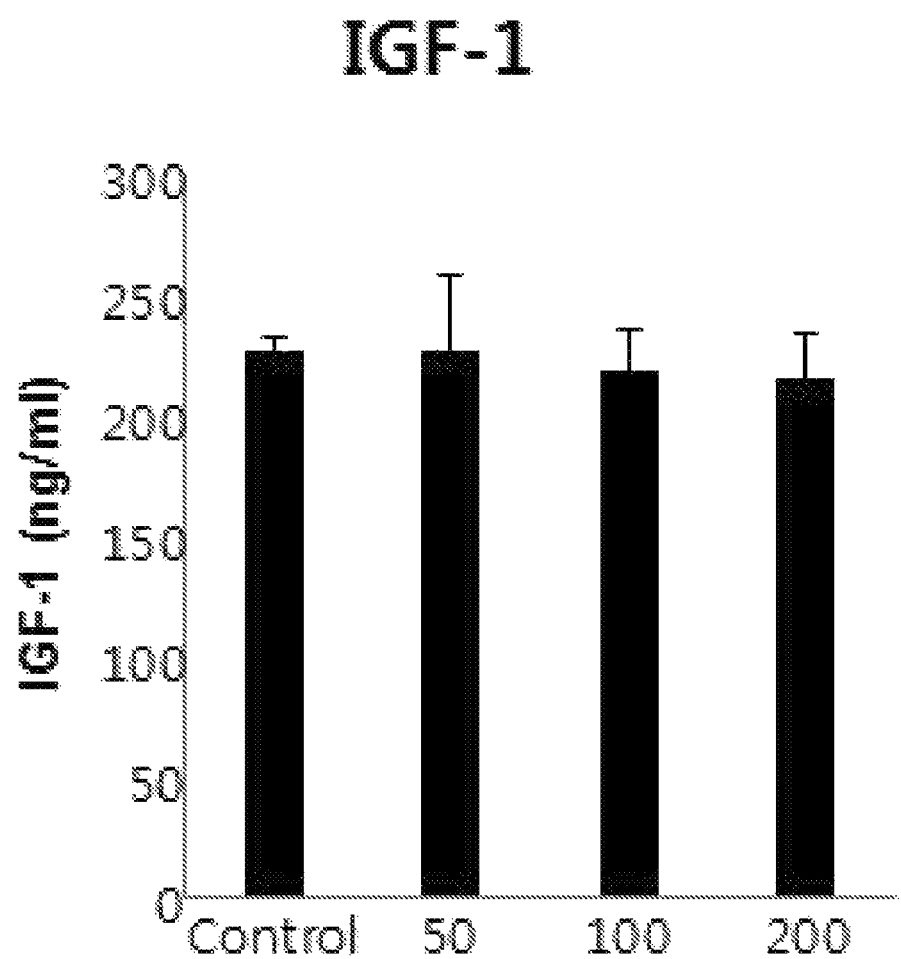
FIG. 14 shows the results of examining the effect of the extract of the present invention on blood IGF-1 level.

The test groups (50 mg/kg, 100 mg/kg, and 200 mg/kg) showed IGF-1 levels of 197.91±25.69 ng/ml, 190.64±20.17 ng/ml and 185.82±9.57 ng/ml, respectively (see FIG. 14). The control group showed an IGF-1 level of 230.76±12.12 ng/ml, which was not greatly different from those of the test groups.

2-14: IGFBP-3

Figure 15:
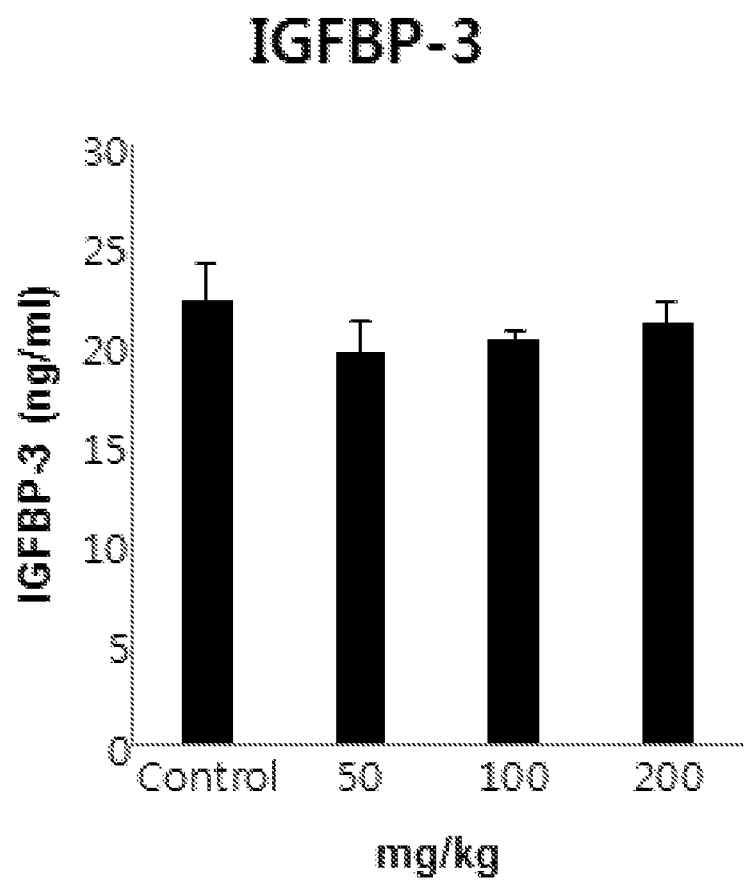
FIG. 15 shows the results of examining the effect of the extract of the present invention on blood IGF-3 level.

The test groups (50 mg/kg, 100 mg/kg, and 200 mg/kg) showed IGFBP-3 levels of 19.65±1.49 ng/ml, 20.27±0.45 ng/ml and 21.10±1.05 ng/ml, respectively (see FIG. 15). The control group showed an IGFBP-3 level of 22.22±1.05 ng/ml, which was not greatly different from those of the test groups.

2-15: ALP

Figure 16:
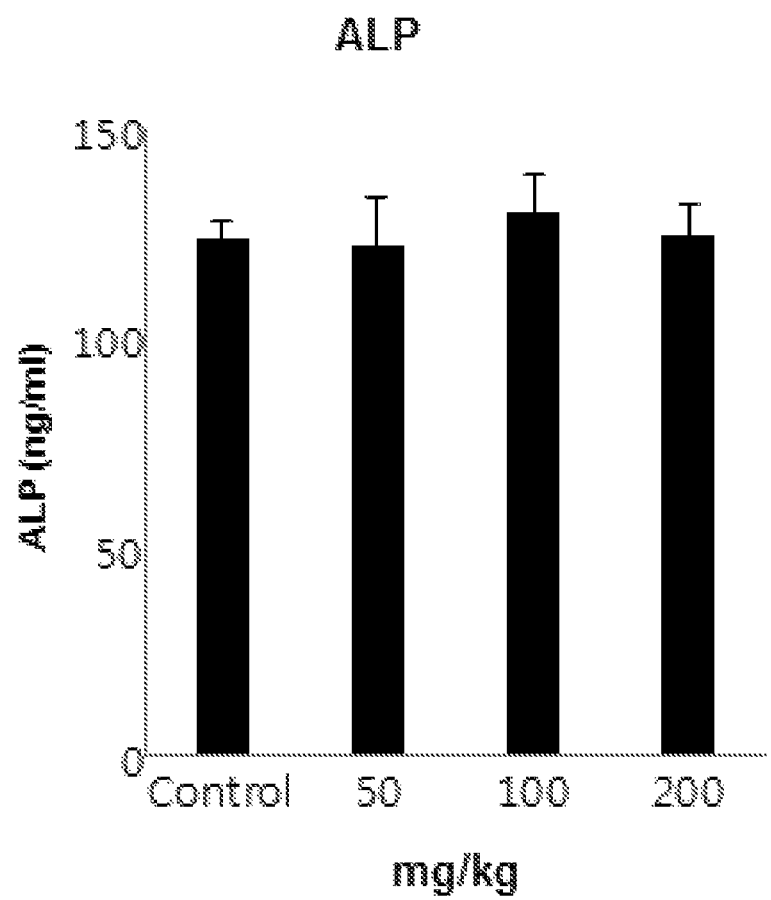
FIG. 16 shows the results of examining the effect of the extract of the present invention on blood ALP level.

The test groups (50 mg/kg, 100 mg/kg, and 200 mg/kg) showed ALP levels of 126.19±3.35 ng/ml, 124.79±4.28 ng/ml, and 119.89±2.18 ng/ml, respectively (see FIG. 16). The control group showed an ALP level of 123.54±4.81 ng/ml, which was not greatly different from those of the test groups.

2-16: Osteocalcin

Figure 17:
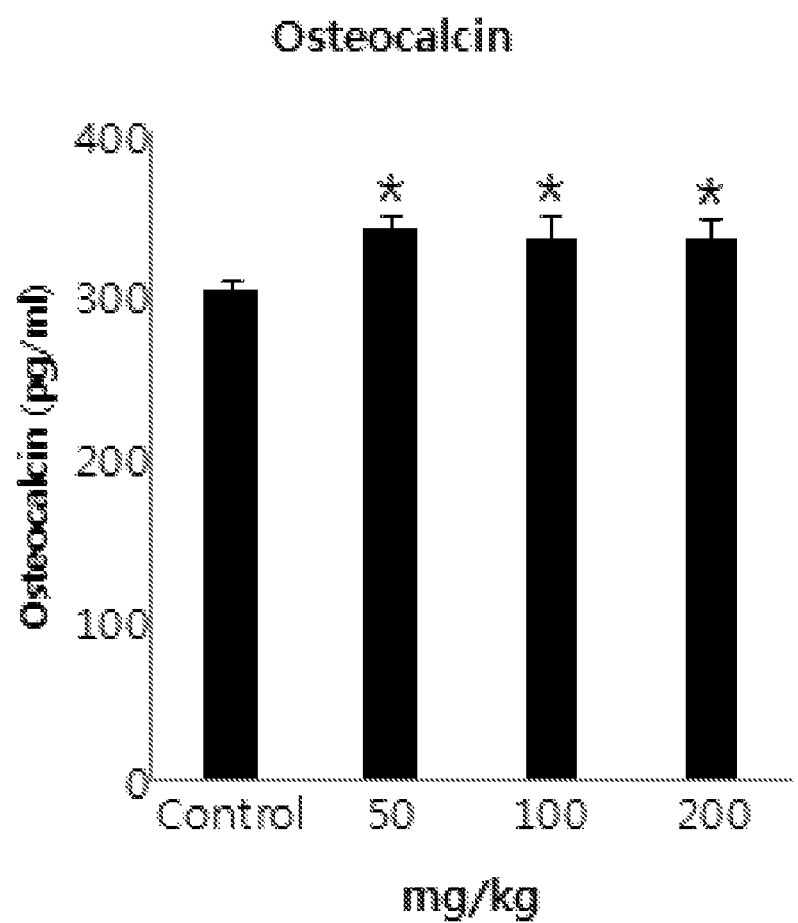
FIG. 17 shows the results of examining the effect of the extract of the present invention on blood osteocalcin level.

The test groups (50 mg/kg, 100 mg/kg, and 200 mg/kg) showed osteocalcin levels of 306.90±18.19 pg/ml, 335.91±14.46 pg/ml and 326.83±12.55 pg/ml, respectively (see FIG. 17). The control group showed an osteocalcin level of 303.30±4.79 pg/ml. Thus, it could be seen that the osteocalcin level significantly increased in the test groups compared to the control group.

2-17. Bone Mineral Density (BMD)

Figure 18:
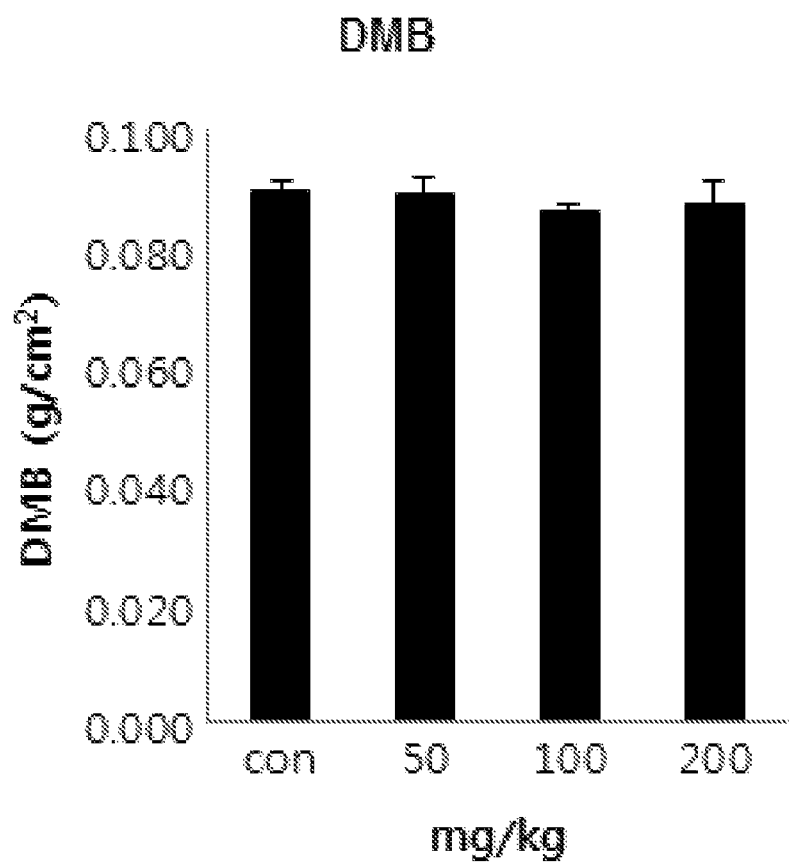
FIG. 18 shows the results of examining the effect of the extract of the present invention on bone mineral density.

The test groups (50 mg/kg, 100 mg/kg, and 200 mg/kg) showed BMD levels of 0.088±0.003 g/cm$^3$, 0.088±0.002 g/cm$^3$, and 0.089±0.003 g/cm$^3$, respectively (see FIG. 18). The control group showed a BMD level of 0.090±0.002 g/cm$^3$, which was not greatly different from those of the test groups.

2-18. Estradiol

Figure 19:
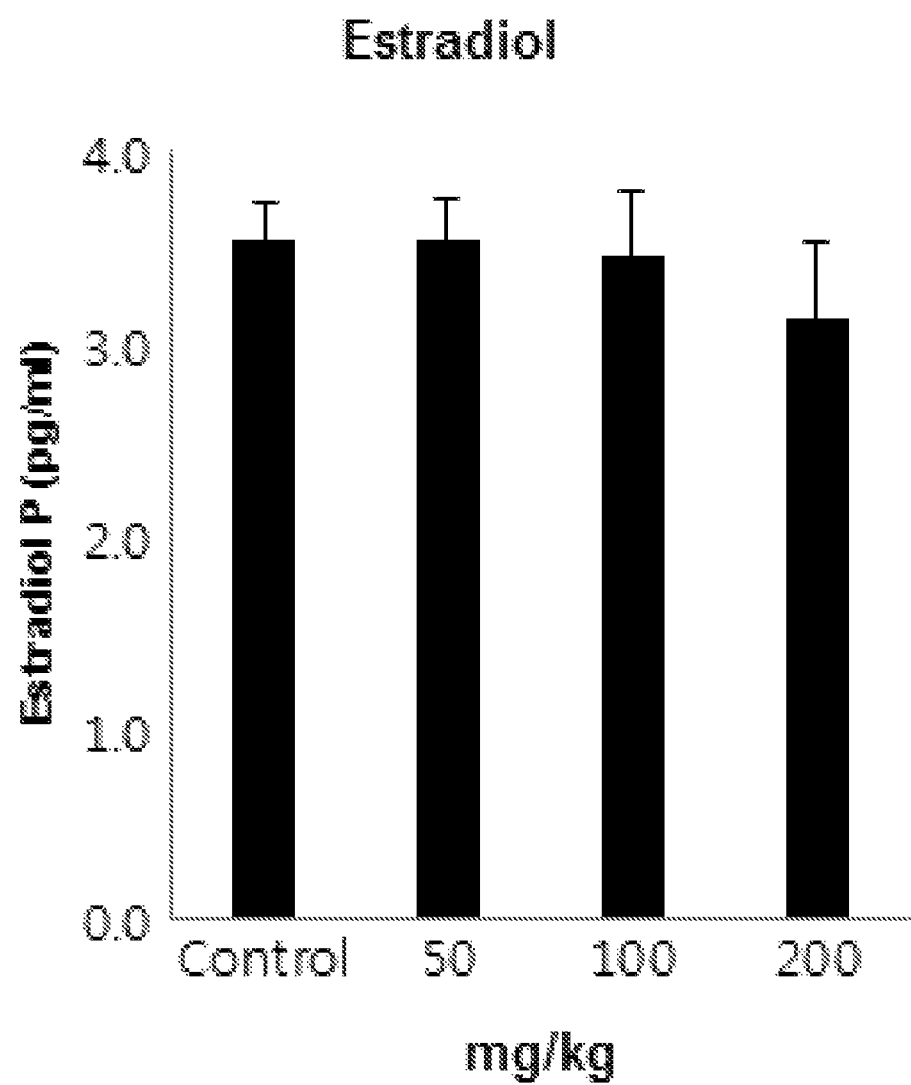
FIG. 19 shows the results of examining the effect of the extract of the present invention on blood estradiol level.

The test groups (50 mg/kg, 100 mg/kg, and 200 mg/kg) showed estradiol levels of 3.54±0.19 pg/ml, 3.45±3.5 pg/ml and 3.12±0.39 pg/ml, respectively (see FIG. 19). The control group showed an estradiol level of 3.53±0.21 pg/ml, which was similar to or somewhat higher than those of the test groups.

2-19: Luteinizing Hormone

Figure 20:
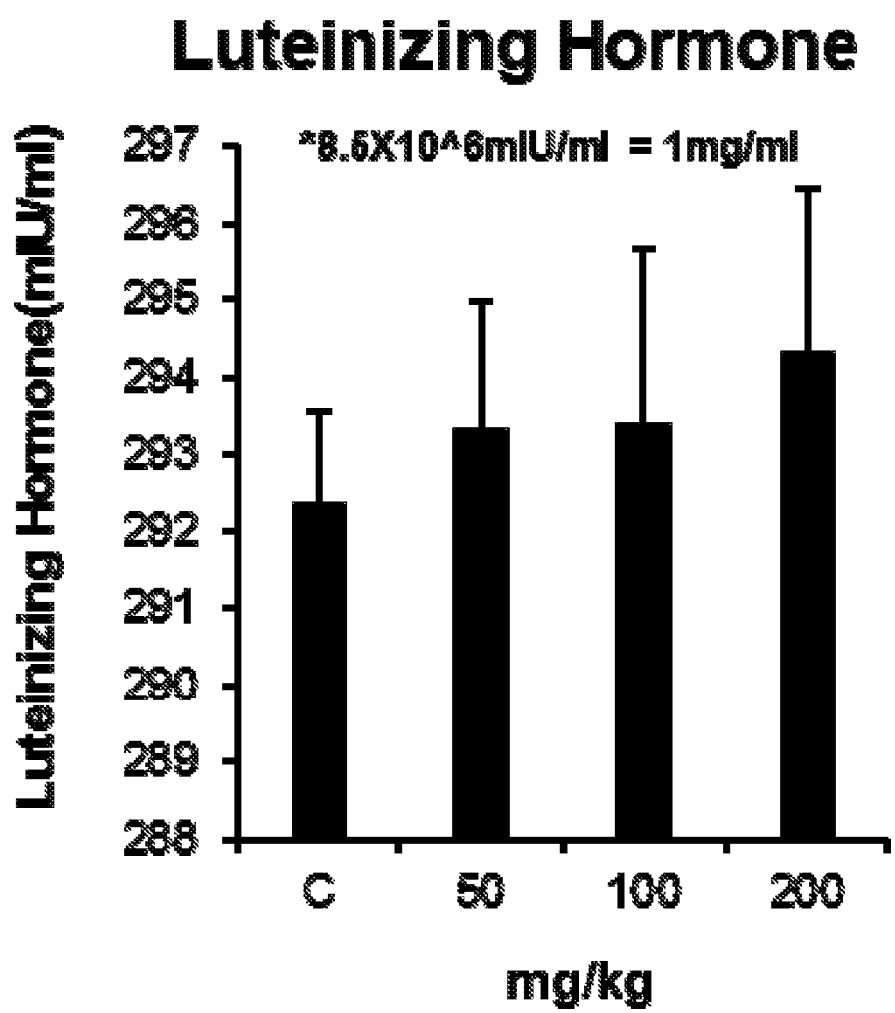
FIG. 20 shows the results of examining the effect of the extract of the present invention on blood luteinizing hormone level.

The test groups (50 mg/kg, 100 mg/kg, and 200 mg/kg) showed luteinizing hormone levels of 293.33±1.63 mIU/ml, 293.4±2.26 mIU/ml and 294.33±2.13 mIU/ml, respectively (see FIG. 20). The control group showed a luteinizing hormone level of 292.33±1.23 mIU/ml. Thus, it could be seen that the luteinizing hormone levels of the test groups were similar to or somewhat higher that of the control group, but this difference was not significant.

2-20. Follicle Stimulating Hormone

Figure 21:
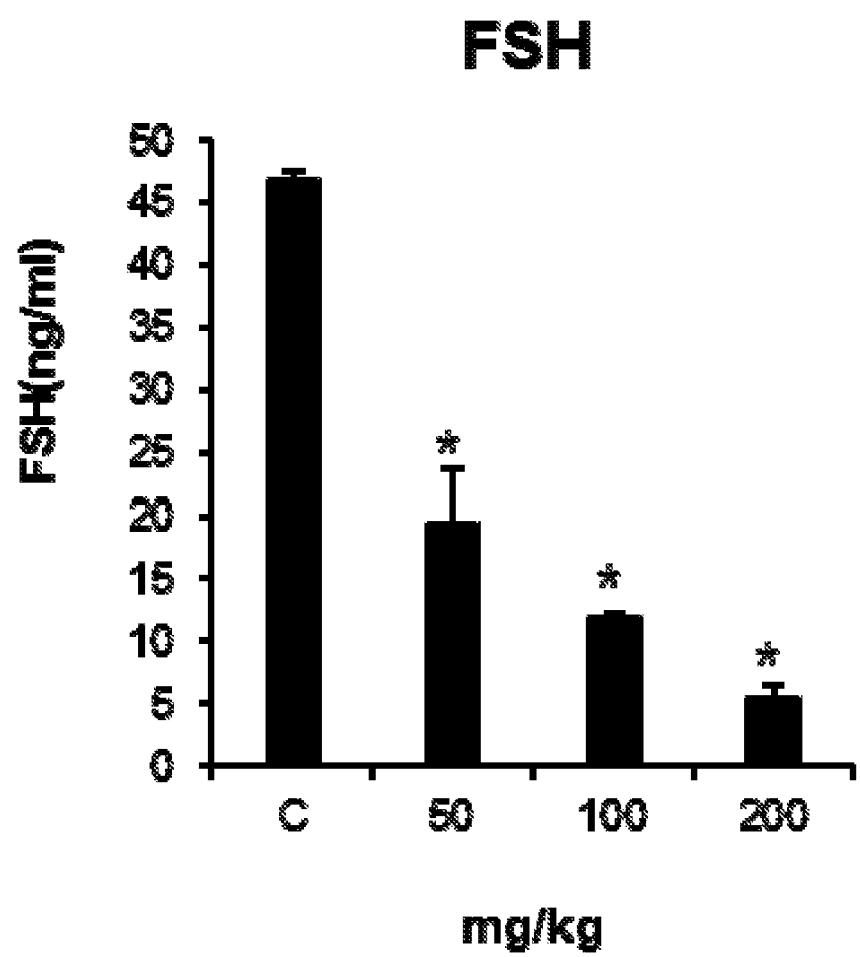
FIG. 21 shows the results of examining the effect of the extract of the present invention on blood follicle-stimulating hormone level.

The test groups (50 mg/kg, 100 mg/kg, and 200 mg/kg) showed follicle stimulating hormone levels of 19.31±4.35 ng/ml, 11.87±0.34 ng/ml and 5.33±1.10 ng/ml (see FIG. 21). The control group showed a follicle stimulating hormone level of 46.73±0.80 ng/ml. Thus, it could be seen that the follicle stimulating hormone levels of the test groups significantly decreased in a concentration-dependent manner compared to that of the control group.

As described above, the composition of the present invention contains a hot-water extract of Coicis Semen and Artemisia capillaris, which can inhibit early ovary growth and the production of follicle stimulating hormone, thereby preventing, alleviating or treating precocious puberty. Particularly, the composition of the present invention has an advantage in that it helpful in height growth, together with the effect of preventing, alleviating or treating precocious puberty as described above. In addition, the composition of the present invention has an advantage in that it is very easily prepared, because the number of different materials used in the composition is smaller than that in conventional herbal formulations.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A pharmaceutical composition for treating precocious puberty, consisting of, as an active ingredient, a hot-water extract of *Coicis* Semen and *Artemisia capillaris*.

2. The pharmaceutical composition of claim 1, wherein the hot-water extract is prepared by adding a 10-20-fold weight of water to *Coicis* Semen and *Artemisia capillaris* mixed at a weight ratio of 2:3 to 3:2, thereby obtaining a mixture, and extracting the mixture at a temperature of 80 to 110° C. for 2 to 4 hours, followed by concentration.

3. The pharmaceutical composition of claim 1, wherein the composition inhibits early ovary growth, inhibits follicle-stimulating hormone production, and increases body length.

4. A food composition for alleviating precocious puberty, consisting of, as an active ingredient, a hot-water extract of *Coicis* Semen and *Artemisia capillaris*.

5. The food composition of claim 4, wherein the hot-water extract is prepared by adding a 10-20-fold weight of water to *Coicis* Semen and *Artemisia capillaris* mixed at a weight ratio of 2:3 to 3:2, thereby obtaining a mixture, and extracting the mixture at a temperature of 80 to 110° C. for 2 to 4 hours, followed by concentration.

6. The food composition of claim 4, wherein the composition inhibits early ovary growth, inhibits follicle-stimulating hormone production, and increases body length.

* * * * *